United States Patent [19]
Voss et al.

[11] Patent Number: 5,968,982
[45] Date of Patent: Oct. 19, 1999

[54] 2,2-DICHLOROALKANECARBOXYLIC ACIDS, PROCESSES FOR THEIR PRODUCTION AND PHARMACEUTICAL AGENTS CONTAINING THESE

[75] Inventors: Edgar Voss, Viernheim; Johannes Pill, Leimen; Peter Freund, Ketsch, all of Germany

[73] Assignee: Roche Diagnostics GmbH, Mannheim, Germany

[21] Appl. No.: 08/817,925

[22] PCT Filed: Nov. 9, 1995

[86] PCT No.: PCT/EP95/04413

§ 371 Date: Jul. 8, 1997

§ 102(e) Date: Jul. 8, 1997

[87] PCT Pub. No.: WO96/15784

PCT Pub. Date: May 30, 1996

[30] Foreign Application Priority Data

Nov. 9, 1994 [DE] Germany .................. 44 39 947

[51] Int. Cl.[6] ............................................. A01N 37/00
[52] U.S. Cl. .................. 514/558; 514/557; 514/559; 514/866; 534/225; 534/226
[58] Field of Search ................... 534/225, 226; 514/557, 558, 559, 860

[56] References Cited

FOREIGN PATENT DOCUMENTS 0 081 930 A1  6/1983  European Pat. Off. .

WO 88/02746  4/1988  WIPO .
WO 94/02128  2/1994  WIPO .

OTHER PUBLICATIONS

J. Med. Chem. 1989, 32, pp. 2072–2084; Jacob Bar–Tana, et al; Nov. 22, 1988.

Bull. Soc. Chim. Belg. vol. 97(7) 1988; pp. 525–533; De Buyck et al.

Ind. Eng. Chem. Res. 1992, 31, pp. 2425–2437; Paatero, et al.

Bull. Chem. Soc. Jpn., 67, pp. 1622–1626 (1994); M. Boni, et al.

Tetrahedran Lett, 1994, pp. 2961–2964: Bellesia et al.

*Primary Examiner*—Deborah D Carr
*Attorney, Agent, or Firm*—Nikaido Marmelstein Murray & Oram, llp.

[57] ABSTRACT

Pharmaceutical agents for treating diabetus mellitus which contain a compound of formula I

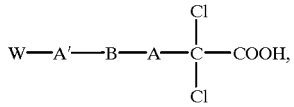

as the active substance, in which A, B, A' and W have the meanings stated in the claims, new compounds of formula I as well as processes for their production.

16 Claims, No Drawings

2,2-DICHLOROALKANECARBOXYLIC ACIDS, PROCESSES FOR THEIR PRODUCTION AND PHARMACEUTICAL AGENTS CONTAINING THESE

This application is a 371 of PCT/EP95/04413 filed Nov. 9, 1995.

The present invention concerns 2,2-dichloroalkanecarboxylic acids, processes for their production and pharmaceutical agents containing these compounds.

The invention concerns 2,2-dichloroalkanecarboxylic acids of the general formula I

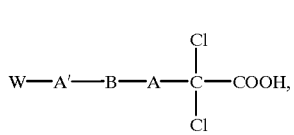

in which
A denotes an alkylene chain with 5–20 carbon atoms,
A' denotes a valency dash, a vinylene or acetylene group or an alkylene chain with 1–10 carbon atoms,
B denotes a valency dash, a methylene group, sulphur, oxygen or the group $NR^1$, in which
  $R^1$ can be hydrogen, benzyl, phenyl or a $C_1$–$C_4$ alkyl residue, a carbonyl, sulfonamide, sulfoxide or sulfonyl group, an E- or Z-vinylene or an acetylene group, a $CR^2R^3$ group, in which
  $R^2$ can be hydrogen, a $C_1$–$C_4$ alkyl residue or phenyl,
  $R^3$ can be a $C_1$–$C_4$ alkyl residue, benzyl, phenyl, hydroxy or a group $NR^4R^5$, in which
  $R^4$ can be hydrogen, benzyl, phenyl or a $C_1$–$C_4$ alkyl residue and
  $R^5$ can be hydrogen or a $C_1$–$C_4$ alkyl residue,
a group Y-Z-Y, in which
  Y can be sulphur or oxygen,
  Z can be an alkyl chain $(CH_2)_n$ and n can be 1–5, and
W denotes a halogen atom; a cyano or thiocyanato group; an aminocarbonyl group, a methyl, isopropyl or tert.-butyl residue; a $C_3$–$C_8$ cycloalkyl residue which can be unsubstituted or be substituted by phenyl or $C_1$–$C_4$ alkyl; a cyclohexenyl or cyclopentenyl residue, a phenyl ring which can be substituted by one or any combination of the following substituents: $C_1$–$C_4$ alkyl, $C_1$–$C_4$ alkoxy, $C_1$–$C_4$ alkylthio, $C_1$–$C_4$ alkylsulfinyl, $C_1$–$C_4$ alkylsulfonyl, trifluoromethyl, nitro, amino, hydroxy, cyano, mercapto, sulfonamino, acetylamino, carboxy, phenoxy, benzyloxy, phenyl, benzoyl, carboxy-$C_1$–$C_4$ alkyl, methylenedioxy, ethylenedioxy, fluorine, chlorine, bromine, iodine, carboxymethoxy, carboxyethoxy, acetoxy, acetyl, propionyl, a $NR^6R^7$ group, in which $R^6$ denotes hydrogen, $C_1$–$C_4$ alkyl or benzyl and $R^7$ denotes hydrogen, $C_1$–$C_4$ alkyl, benzyl, phenyl, or benzoyl whereby the respective aromatic ring is optionally unsubstituted, or can be substituted by one or any combination of the following substituents: halogen, hydroxy or $C_1$–$C_4$ alkoxy; furthermore an α- or β-naphthyl ring which can be substituted by methyl, hydroxy, methoxy, carboxy, methoxycarbonyl, ethoxycarbonyl, cyano, acetyl, chlorine or bromine or a tetrahydronaphthyl residue,
as well as their physiologically tolerated salts or esters and substances which are hydrolyzed or metabolized in vivo to compounds of the general formula I. If chiral compounds are formed by substitution of the alkylene chain in I with the described residues, the substances in the R as well as S configuration are a subject matter of the invention $C_1$–$C_4$-alkyl residues denotes for branched or unbranched alkyl groups.

Compounds of formula I have valuable pharmacological properties. They normalize an increased glucose level without a concomitant risk of hypoglycaemia and are thus excellently suited for the therapy of diabetes mellitus.

Previous mechanisms of action of oral antidiabetics such as the generally used sulfonyl ureas are based on an increased release of insulin from the β-cells of the pancreas, a mechanism which in the long term leads to the complete exhaustion of the endogenous production of insulin in diabetics. The modern view of the pathobiochemistry of adult-onset diabetes therefore emphasizes the need to treat the peripheral insulin resistance that is present in this case.

Compounds of formula I improve glucose utilization e.g in muscle, they decrease hyperinsulinaemia by increasing insulin sensitivity and thus comply exactly with the therapy concept.

Diabetics often suffer from a complete derangement of the entire metabolic condition characterized by hyperlipidaemia, increase in cholesterol, hypertension, adiposity and hyperinsulinaemia, a clinical picture which is denoted metabolic syndrome or syndrome X and leads to a very wide range of late complications. Apart from decreasing hyperinsulinaemia compounds of the general formula I additionally decrease triglycerides, cholesterol and fibrinogen and are thus excellently suitable for treating the metabolic syndrome.

Compounds of the general formula I in which W denotes a chlorine atom and A-B-A' denotes an alkylene chain —$(CH_2)_n$— have already been described with no information about a pharmacological effect. Thus the ethyl ester of 2,2,8-trichlorooctanoic acid (n=6) is described in Doklady Akad. Nauk S.S.S.R. 127, 1027 (1959). Izvest. Akad. Nauk S.S.S.R. 1960, 1215 describes the synthesis of 2,2,8-trichloro-octanoic acid (n=6), 2,2,6-trichlorohexanoic acid (n=4) and 2,2,6-trichloro-heptanoic acid (n=5).

In addition compounds of the general formula I in which W denotes a methyl group and A-B-A' denotes an alkylene chain $(CH_2)_n$ are also known and are found as the main products or by-products in chlorination reactions without their use as pharmaceutical agents having been described up to now. Ind. Eng. Chem. Res. 114, 2425 (1992): 2,2-dichlorodecanoic acid, 2,2-dichlorooctanoic acid and 2,2-dichlorotetradecanoic acid. Bull. Soc. Chim. Belg. 97, 525 (1988): 2,2-dichlorodecanoic acid, 2,2-dichloro-octanoic acid, 2,2-dichlorooctadecanoic acid, 2,2-dichlorododecanoic acid, 2,2-dichlorohexadecanoic acid and 2,2-dichlorotetradecanoic acid. Eur. Pat. 167 202: 2,2-dichlorooctanoic acid and 2,2-dichlorononanoic acid. Wear 3, 200 (1960): 2,2-dichlorooctadecanoic acid. Eur. Pat. 87, 835: 2,2-dichlorooctadecanoic acid. Izv. Vyssh. Uchebn. Zaved, Khim. Khim. Tekhnol. 18, 674 (1975): 2,2-dichlorooctadecanoic acid and 2,2-dichlorononanoic acid. The German laid-open patent application 2,264,234: 2,2-dichloro-tetradecanoic acid. U.S. Pat. No. 3,573,332: 2,2-dichlorododecanoic acid. Can J. Chem. 36, 440 (1958): 2,2-dichlorododecanoic acid.

Preferred compounds of the general formula I are compounds, in which
  A denotes an alkylene chain with 8–14, preferably 10–12 carbon atoms,
  A' denotes a valency dash, vinylene or acetylene,
  B denotes a valency dash, a methylene group, oxygen, sulphur, sulfoxide or sulfonyl and W denotes a $C_3$–$C_8$ cycloalkyl or a phenyl residue which can be substituted if desired in particular 4-chlorophenyl, 4-methylthiophenyl, 4-$C_1$–$C_4$-alkylphenyl, 4-methylsulfonylphenyl.

The alkylene chain A or A' is preferably straight-chained but it can also be branched.

Halogen is understood as fluorine, chlorine, bromine or iodine. The $C_3$–$C_8$-cycloalkyl residues denote cyclopropyl, cyclobutyl, cyclopentyl, cyclohexyl, cycloheptyl or cyclooctyl.

Examples of physiologically applicable salts of the compounds of formula I are alkali metal, alkaline-earth metal, ammonium and alkylammonium salts such as a Na, K, Mg, Ca or tetramethylammonium salt.

The carboxylic acid derivatives of the general formula I can be administered orally or parenterally in a liquid or solid form. Water is preferably used as the injection medium which contains the stabilizing agents, solubilizers and/or buffers which are common in injection solutions. Such additives are for example tartrate or borate buffer, ethanol, dimethylsulfoxide, complexing agents (such as ethylenediaminetetraacetic acid), high molecular polymers (such as liquid polyethylene oxide) to regulate viscosity or polyethylene derivatives of sorbitol anhydrides. Solid carrier substances are for example starch, lactose, mannitol, methylcellulose, talcum, highly dispersed silicic acid, higher molecular polymers (such as polyethylene glycols). For oral application suitable preparations can contain flavourings and sweeteners if desired.

The administered dose depends on the age, state of health and weight of the recipient, the extent of the disease, the type of additional treatments that may be carried out at the same time and the type of desired effect. The daily dose of the active compound is usually 0.1 to 50 mg/kg body weight. Usually 0.5 to 40 and preferably 1.0 to 20 mg/kg/day are effective in one or several administrations per day in order to obtain the desired results.

The present invention also concerns new compounds of formula I, in which

A denotes an alkylene chain with 5–20 carbon atoms,

A' denotes a valency dash, a vinylene or acetylene group or an alkylene chain with 1–10 carbon atoms, B denotes sulfonyl, a valency dash, sulphur, sulfoxid, methylene, sulfonamide, oxygen or the group $NR^1$ in which $R^1$ can be hydrogen, benzyl, phenyl or a $C_1$–$C_4$ alkyl residue, a carbonyl, sulfonamide, sulfoxide or sulfone group, an E- or Z-vinylene or an acetylene group, a $CR^2R^3$ group, in which $R^2$ can be hydrogen, a $C_1$–$C_4$ alkyl residue or phenyl, $R^3$ can be a $C_1$–$C_4$ alkyl residue, benzyl, phenyl, hydroxy or a group $NR^4R^5$, in which $R^4$ can be hydrogen, benzyl, phenyl or a $C_1$–$C_4$ alkyl residue and $R^5$ can be hydrogen or a $C_1$–$C_4$ alkyl residue, a group Y-Z-Y, in which Y can be sulphur or oxygen, Z can be an alkyl chain $(CH_2)_n$ and n can be 1–5, and W denotes bromine, a cyano or thiocyanato group, methyl, isopropyl or tert.-butyl residue, a $C_3$–$C_8$ cycloalkyl residue which can be unsubstituted or be substituted by phenyl or $C_1$–$C_4$ alkyl; a cyclohexenyl or cyclopentenyl residue, a phenyl ring which can be substituted by one or any combination of the following substituents: $C_1$–$C_4$ alkyl, $C_1$–$C_4$ alkoxy, $C_1$–$C_4$ alkylthio, $C_1$–$C_4$ alkylsulfinyl, $C_1$–$C_4$-alkylsulfonyl, trifluoromethyl, nitro, amino, hydroxy, cyano, mercapto, sulfonamino, acetylamino, carboxy, phenoxy, benzyloxy, phenyl, benzoyl, carboxy-$C_1$–$C_4$ alkyl, methylenedioxy, ethylenedioxy, fluorine, chlorine, bromine, iodine, carboxymethoxy, carboxyethoxy, acetoxy, acetyl, propionyl, a $NR^6R^7$ group in which $R^6$ denotes hydrogen, $C_1$–$C_4$ alkyl or benzyl and $R^7$ denotes hydrogen, $C_1$–$C_4$ alkyl, benzyl, phenyl, or benzoyl whereby the respective aromatic ring is optionally unsubstituted, or can be substituted by on or any combination of the following substituents: halogen, hydroxy or $C_1$–$C_4$ alkoxy; furthermore an α- or β-naphthyl ring which can be substituted by methyl, hydroxy, methoxy, carboxy, methoxycarbonyl, ethoxycarbonyl, cyano, acetyl, chlorine or bromine or a tetrahydronaphthyl residue, as well as physiologically tolerated salts thereof or esters and substances which are hydrolyzed or metabolized in vivo to compounds of the general formula I.

The compounds of the general formula I in which A, A', B and W have the meanings stated above are produced by reacting a halogen compound of the general formula II

X—A—B—A'—W       (II)

with dichloroacetic acid or esters of dichloroacetic acid in the presence of strong bases. The reaction is usually carried out in solvents such as diethyl ether, tetrahydrofuran, dimethoxyethane, diethylene glycol dimethyl ether or t-butyl dimethyl ether at temperatures between –80° C. and –20° C. A preferred base is lithium diisopropylamide (LDA). The products are usually purified by flash chromatography on silica gel and/or recrystallizing the sodium salts from alcohols such as methanol, ethanol or isopropanol.

The compounds of formula II are known from the literature or can be prepared according to known processes. Thus for example the halogen compounds can be synthesized by the Wittig reaction of an aromatic or aliphatic aldehyde W—CHO with the phosphonium salt of α,ω-dihalogen compound, if desired followed by subsequent catalytic hydrogenation of the double bond that is formed. Alternatively a W—Br composed of aryl or alkyl bromide can be converted by magnesium into the Grignard compound and coupled to α,ω-dihalogen compounds under cuprate catalysis according to Schlosser ("Angew. Chem. 86, 50 (1974)).

Halogen compounds of the general formula II in which W denotes an aryl, alkyl or cycloalkyl residue are obtained by converting the corresponding bromide compound W—Br by magnesium into the Grignard compound and coupling to an α,ω-dihalogen compound under cuprate catalysis according to Schlosser ("Angew. Chem. 86, 50 (1974)).

Compounds II in which A' or B correspond to an acetylene group are synthesized by reacting the acetylene compound W—C≡C—H or W—A'—C≡C—H with α,ω-dibromoalkanes in liquid ammonia in the presence of sodium amide or in dioxane in the presence of butyllithium. Substances of formula II in which B or A' denotes a vinylene group can be obtained by hydrogenation of the triple bond according to known methods e.g. on a catalyst according to Lindlar.

If B denotes a sulphur atom in compounds of formula II, these are prepared by reacting the thiols W—SH or W—A'—SH with the ω-bromo-2,2-dichlorocarboxylic acid esters described in this invention. Dipolar aprotic solvents, preferably dimethylformamide are suitable for carrying out this reaction in the presence of inorganic bases such as sodium hydride or potassium carbonate. The thioethers obtained can be converted into sulfoxides or sulfones in a well-known manner by oxidation with 3-chloro-perbenzoic acid or hydrogen peroxide.

Compounds of the general formula II in which B denotes oxygen or nitrogen are prepared by reacting the alcohols, phenols W—A'—OH or amines W—A'NHR$^1$ with α,ω-dibromoalkanes in which the reaction is usually carried out in dimethylformamide or dimethylsulfoxide in the presence of bases such as sodium hydride, potassium hydroxide, triethylamine, potassium carbonate or pyridine at temperatures of 20–120° C.

In addition to the compounds mentioned in the examples the following compounds of formula I also come into consideration within the sense of the present invention which can also be present as salts or esters 1. 2,2-Dichloro-14-(3,5-di-tert-butyl-4-hydroxy-phenyl)-tetradecanoic acid
2. 2,2-Dichloro-14-(3,5-dimethyl-4-hydroxyphenyl)-tetradecanoic acid
3. 2,2-Dichloro-14-(3-trifluoromethyl-phenyl)-tetradecanoic acid
4. 2,2-Dichloro-14-(2-methoxy-phenyl)-tetradecanoic acid
5. 2,2-Dichloro-14-(2-chlorophenyl)-tetradecanoic acid
6. 14-(4-Carboxyphenyl)-2,2-dichlorotetradecanoic acid
7. 12-(4-Carboxymethoxy-phenyl)-2,2-dichlorododecanoic acid
8. 2,2-Dichloro-14-cyclohex-2-enyl-tetradecanoic acid
9. 2,2-Dichloro-14-cyclopentyltetradecanoic acid
10. Cis-14-(4-tert.-Butyl-cyclohexyl)-2,2-dichloro-tetradecanoic acid
11. 2,2-Dichloro-12-(5,6,7,8-tetrahydronaphth-1-yl)-dodecanoic acid
12. 2,2-Dichloro-14-(4-cyanophenyl)-tetradecanoic acid
13. 12-Biphen-4-yl-2,2-dichlorododecanoic acid
14. 10-(4-Benzyloxyphenyl)-2,2-dichlorodecanoic acid
15. 2,2-Dichloro-12-(toluene-4-sulfonylamino)-dodecanoic acid
16. 2,2-Dichloro-12-(4-phenoxyphenyl)-dodecanoic acid
17. 14-(4-Acetylaminophenyl)-2,2-dichlorotetradecanoic acid
18. 10-(4-Benzyl-phenyl)-2,2-dichlorodecanoic acid
19. 2,2-Dichloro-17,17-dimethyl-octadecanoic acid
20. 2,2-Dichloro-14-(4-methyl-phenyl)-14-oxo-tetradecanoic acid
21. 2,2-Dichloro-14-(4-fluorophenyl)-tetradecanoic acid
22. 2,2-Dichloro-12-(4-methylsulfonylphenyl)-dodecanoic acid
23. 12-(4-tert.-Butylphenyl)-2,2-dichlorododecanoic acid
24. 12-(4-tert.-Butylphenoxy)-2,2-dichlorododecanoic acid
25. 2,2-Dichloro-15-phenyl-pentadecanoic acid
26. 2,2-Dichloro-16-phenyl-hexadecanoic acid
27. 2,2-Dichloro-13-phenyltridecanoic acid
28. 2,2-Dichloro-14-cyclohexyl-tetradecanoic acid
29. 2,2-Dichloro-14-(4-methoxy-phenyl)-14-oxo-tetradecanoic acid

PRACTICAL EXAMPLES

Example 1

12-Bromo-2,2-dichlorododecanoic acid (1)

A solution of 6.41 g (49.7 mmol) dichloroacetic acid in 20 ml THF is added dropwise at −70° C. within 30 minutes to a solution of lithium diisopropylamide under a nitrogen atmosphere prepared at 0° C. in 150 ml tetrahydrofuran from 11.2 g (110 mmol) diisopropylamine and 66.0 ml (105 mmol) butyllithium (1.6 M in hexane). It was allowed to stir for a further 30 minutes at −70° C. and the clear yellow solution was admixed with 15.0 g (50.0 mmol) 1,10 dibromodecane dissolved in 30 ml THF and the temperature was kept for 6 hours between −50 and −35° C. The concentration precipitate that first formed dissolved again in this process. For the processing 200 ml 3 N HCl was added and it was extracted with 200 ml ethyl acetate. The organic phase was washed with 3 N HCl and saturated NaCl solution and the aqueous phase was again extracted with 200 ml ethyl acetate. The combined organic phases were dried over sodium sulfate and the solvent was removed by distillation. Flash chromatography of the residue on silica gel (mobile solvent: petroleum ether/ethyl acetate 4:1, 1% glacial acetic acid) yielded 8.3 g (48%) 1, melting point 49–51° C. (isohexane).

Example 2

14-Bromo-2,2-dichlorotetradecanoic acid (2)

Analogously to example 1 from 50.0 g (152 mmol) 1,12-dibromododecane and 39.3 g (305 mmol) dichloroacetic acid. Yield 11.9 g (21%), melting point 59–60° C.

Example 3

14-Bromo-2,2-dichlorotetradecanoic acid ethyl ester (3)

One drop of dimethylformamide and 1.34 g (10.5 mmol) oxalyl chloride was added to a solution of 3.30 g (8.77 mmol) 2 in 40 ml dichloromethane. After 30 minutes excess oxalyl chloride was removed in a stream of nitrogen. Subsequently a mixture of 0.97 g (21.1 mmol) ethanol and 2.13 g (21.1 mmol) triethylamine was added dropwise at 0° C. It was allowed to reach room temperature and it was stirred for a further 30 minutes. After adding 60 ml water it was extracted with methylene chloride, washed with 0.5 N HCl and water, dried over sodium sulfate and the solvent was removed. Yield 3.38 g (95%) colourless oil.

Example 4

16-Bromo-2,2-dichlorohexadecanoic acid (4)

Analogously to example 1 from 2.0 g (5.6 mmol) 1,14-dibromotetradecane and 2.3 g (22.5 mmol) dichloroacetic acid. Yield 0.58 g (23%), melting point 61–63° C.

Example 5

7-Bromo-2,2-dichloroheptanoic acid (5)

24.3 g (33.6 ml, 0.240 mol) diisopropylamine was dissolved in 100 ml THF while stirring in a nitrogen atmosphere and it was added dropwise at −50° C. to 100 ml (0.240 mol) of a 2.40 M solution of butyllithium in hexane. It was allowed to reach −10° C. for 10 minutes, a solution of 15.5 g (0.120 mol) dichloroacetic acid in 20 ml THF was then added dropwise at −75° C., it was stirred for 25 minutes at −75° C. and subsequently 93.5 g (55.0 ml, 0.41 mol) 1,5-dibromopentane in 50 ml THF was added in such a way that the temperature increased to −40° C. After 2.5 hours at −40° C. it was hydrolyzed with 10 ml 6 N HCl and the precipitate that formed was dissolved with 20 ml water. The organic phase was washed twice with a small amount of water, dried over magnesium sulfate and the solvent was removed in a vacuum. Flash chromatography of the residue on silica gel (mobile solvent: ethyl acetate/heptane 1:10) yielded 19.5 g (59%) 7-bromo-2,2-dichloroheptanoic acid 5 as a colourless oil.

Example 6

7-Bromo-2,2-dichloroheptanoic acid ethyl ester (6)

19.5 g 5 was dissolved in 300 ml ethanol, saturated at 0° C. with hydrochloric acid gas and stirred for a further 5 hours at 0° C. After removing the major amount of ethanol in a vacuum, the residue was taken up in ether, washed with water, dried over magnesium sulfate and the solvent was removed. 21.2 g (98%) 7-bromo-2,2-dichloroheptanoic acid ethyl ester 6 was obtained as a colourless oil.

Example 7

8-Bromo-2,2-dichlorooctanoic acid (7)

Analogously to example 5 from 12.7 g (52.0 mmol) 1,6-dibromohexane and 2.2 g (17.0 mmol) dichloroacetic acid. Yield 7.64 (50%) colourless oil.

Example 8

2,2-Dichloro-12-cyano-dodecanoic acid (8)

A solution of 3.42 g (9.82 mmol) 1 in 5 ml DMSO was quickly added dropwise to a suspension of 393 mg (9.82 mmol) sodium hydride (60% in white oil) in 30 ml DMSO. After the formation of hydrogen is completed, 1.47 g (30.0 mmol) sodium cyanide (dried at 120° C. in a high vacuum) was added and it was heated for 45 minutes to 50–60° C.

After cooling 200 ml ethyl acetate was added and it was acidified with a solution of 10 g iron(Ill) chloride in 3 N HCl. It was washed twice with saturated NaCl solution and the aqueous phase was extracted with ethyl acetate. The combined organic phases were dried over sodium sulfate. After removing the solvent and flash chromatography on silica gel (mobile solvent: petroleum ether/ethyl acetate 4:1, 1% glacial acetic acid) 2.61 g (90%) 8 was obtained as a pale yellow oil.

Example 9

2,2-Dichloro-12-phenoxy-dodecanoic acid (9)

1-Bromo-10-phenoxy-decane (61)

2.90 g (30.8 mmol) phenol and 9.00 g (30.0 mmol) 1,10-dibromodecane were added to a sodium ethanolate solution prepared from 1.20 g (30.0 mmol) NaH (60% in white oil) and 30 ml ethanol. The initial clear pale yellow solution was heated to reflux. A precipitate already began to form after 30 min. It was allowed to cool after 6 hours, 300 ml ethyl acetate was added and it was washed three times with 200 ml saturated saline solution. After drying over sodium sulfate and concentrating on a rotary evaporator, the residue was dissolved in ethanol and stored for 24 hours in a refrigerator. The precipitated product was suction filtered and washed with a small amount of cold ethanol. 6.00 g (64%) 61, melting point 62–64° C.

A solution of 5.84 g (18.6 mmol) 61 was added at –78° C. to an enolate solution prepared analogously to example 1 from 7.60 g (75.0 mmol) diisopropylamine, 46 ml (74 mmol) butyllithium (1.6 M in hexane) and 4.81 g (37.2 mmol) dichloroacetic acid in 80 ml THF and it was allowed to thaw slowly in a cooling bath. After reaching –30° C. is was again cooled to –50° C. and then allowed to reach –20° C. After addition of 50 ml 3 N HCl and 200 ml ethyl acetate it was washed twice with 150 ml 3 N HCl each time and twice with saturated NaCl solution. After drying over sodium sulfate and removing the solvent on a rotary evaporator, it was purified by means of flash chromatography on silica gel (mobile solvent: petroleum ether/isopropanol 96:4, 0.5% glacial acetic acid), 4.25 g (63%) pale yellow oil which soon solidifies to form a wax-like mass.

Example 10

2,2-Dichloro-12-(4-methyl-phenoxy)-dodecanoic acid (10)

1-Bromo-10-(4-methyl-phenoxy)-decane (62)

18 g (60 mmol) 1,10-dibromodecane was added to a phenolate solution prepared from 6.5 g (60 mmol) NaH (60% in white oil) in 60 ml ethanol and it was heated for 6 hours under reflux. A colourless precipitate separated. After addition of 200 ml 3 N HCl and 200 ml ethyl acetate it was washed twice with saturated NaCl solution, dried over sodium sulfate and the solvent was removed by evaporation in a vacuum. The phenyl ether precipitated from the crude product after addition of toluene. The filtrate was distilled and the 150–160° C. (1.3 mbar) fraction was recrystallized from ethyl acetate. Yield 9.75 g 62.

The crude product obtained analogously to example 9 from 5.15 g (40 mmol) dichloroacetic acid and 9.5 g (29 mmol) 62 was freed of polar impurities by flash chromatography (silica gel, mobile solvent: ethyl acetate/petroleum ether 9:1, 1% glacial acetic acid). The oil obtained was taken up in petroleum ether and the sodium salt was precipitated using saturated sodium bicarbonate solution. The acid was liberated again with 3 N HCl after filtration and recrystallization from ethyl acetate, it was extracted with ethyl acetate, dried over sodium sulfate and the solvent was removed by evaporation. Recrystallization of the free acid from petroleum ether yielded 2.4 g (22%) 10, melting point 67–68° C.

Example 11

2,2-Dichloro-12-(4-chlorophenoxy)-dodecanoic acid (11)

1-Bromo-10-(4-chlorophenoxy)-decane (63)

Analogously to the preparation of 62, 13.6 g (65%) 63 was obtained from 7.7 g (60 mmol) 4-chlorophenol and 18 g (60 mmol) 1,10-dibromodecane. 13.3 g (38.0 mmol) 63 was reacted with dichloroacetic acid according to example 9. 5.9 g (50%) 11, melting point 63–64° C. was obtained.

Example 12

2,2-Dichloro-12-(4-methoxy-phenoxy)-dodecanoic acid (12)

1-Bromo-10-(4-methoxy-phenoxy)-decane (64)

8.8 g (43%) 64 melting point 64–66° C. was obtained analogously to the preparation of 62, by reacting 7.5 g (60 mmol) hydroquinone monomethyl ether and 18 g (60 mmol) 1,10-dibromodecane.

An enolate solution prepared from 80.0 mmol lithiumdiisopropylamide and 5.15 g (40.0 mmol) dichloroacetic acid in 50 ml THF was added dropwise within 1 hour at 0–10° C. to a solution of 7.0 g (20 mmol) 64 in 20 ml THF. After stirring for 1 hour it was hydrolyzed with 3 N HCl, admixed with 200 ml ethyl acetate, washed twice with 3 N HCl and once with saturated NaCl solution and the organic phase was concentrated by evaporation in a vacuum. The oily residue was taken up in petroleum ether and admixed with as much saturated $NaCHO_3$ solution until no further $CO_2$ generation was observed. After 30 minutes the precipitate that formed was suction filtered and recrystallized from ethyl acetate. The colourless salt was taken up in ethyl acetate and admixed with 3 N HCl and the organic phase was washed with saturated saline solution.

The oil that was obtained after drying over sodium sulfate and concentration by evaporation was crystallized from petroleum ether. 1.6 g (20%) 12 was obtained as colourless flakes, melting point 68–69° C.

Example 13

2,2-Dichloro-12-phenyl-dodec-11-enoic acid (13)

9-Bromononyltriphenylphosphonium bromide (65)

103 g (0.36 mol) 1,9-dibromononane is stirred at 120° C. and a solution of 11.8 g (0.045 mol) triphenylphosphine in 120 ml toluene is added within 8 hours. After a further 10 hours at 120° C. it is allowed to cool, the supernatant is decanted and the viscous residue is stirred twice with isohexane at 60° C. After drying on a rotary evaporator in a stream of nitrogen 22.4 g (91%) 65 was obtained as a nearly colourless resin.

10-Bromo-1-phenyl-1-decene (66)

2.13 g (3.8 mmol) 65 was dissolved in 200 ml TEF and cooled to –78° C. under a nitrogen atmosphere. 1.53 ml (3.6 mmol) butyllithium (2.45 N in hexane) was added dropwise in the process of which the typical orange-red ylide colour is formed. It was stirred for a further 30 minutes at –78° C. and admixed all at once with 0.40 ml (4.0 mmol) freshly distilled benzaldehyde after which the solution decolourized. The temperature was allowed to rise to 0° C. within 30 minutes and it was admixed with 5 ml saturated ammonium chloride solution. After adding several drops of 2 N HCl the organic phase was separated, the aqueous phase was extracted once with ether and the combined organic phases were washed twice with water. After drying over magnesium sulfate and removing the solvent it was purified by flash chromatography on silica gel (mobile solvent: heptane). 0.86 g (73%) 66, colourless oil.

4.52 g (15.3 mmol) 66 was reacted with 4.34 g (33.7 mmol) dichloroacetic acid analogously to example 9. The preparation was hydrolyzed at –40° C. with 6 N HCl and the concentration precipitate that formed was dissolved by addition of a few ml of water. The organic phase was separated, washed with water, dried over magnesium sulfate and the solvent was removed by evaporation in a vacuum. After flash chromatography on silica gel (mobile solvent: heptane →heptane/ethyl acetate 10:1) 2.32 g (45%) 13 was obtained, melting point 50–52° C.

Example 14

2,2-Dichloro-12-phenyldodecanoic acid (14)

1.09 g (3.18 mmol) 13 was dissolved in 300 ml THF and hydrogenated for 40 minutes at –40° C. at a hydrogen overpressure of 42 mbar after addition of 200 mg 10% $Pd/BaSO_4$. The catalyst is sucked off and 0.95 g (90%) 14 was obtained as a colourless oil after evaporating the remaining solution. 100 mg (0.29 mmol) 14 was dissolved in 1 ml ethanol, cooled in an ice-bath and admixed with a solution of 12 mg (0.29 mmol) sodium hydroxide in 1 ml ethanol. The sodium salt was precipitated by addition of ether and it was allowed to stand for 12 hours in a refrigerator. The precipitate was suction filtered, washed with cold ether and dried in a vacuum. 100 mg (94%) sodium salt of 14, melting point 157–159° C.

Example 15

2,2-Dichloro-12-cyclohexyl-dodecanoic acid (15)

1-Bromo-10-cyclohexyldecane (67)

10 ml (1 mmol) of an orange-red solution of $Li_2CuCl_4$ prepared from 1.344 g (10.0 mmol) $CuCl_2$ and 0.848 g (20 mmol) anhydrous lithium chloride and 100 ml THF was added to a solution of 18.0 g (60.0 mmol) 1,10-dibromodecane in 20 ml THF.

Subsequently a Grignard solution formed from 2.10 g magnesium and 11.7 g (72.0 mmol) cyclohexyl bromide was added dropwise within 1 h at 0° C. It was allowed to thaw during which the preparation became dark coloured and a precipitate precipitated. After stirring for 20 h 50 ml saturated ammonium chloride solution and 100 ml ethyl acetate were added, the phases were separated, it was washed twice with saturated NaCl solution, the organic phase was dried over sodium sulfate, the solvent was removed on a rotary evaporator and the residue was fractionated by vacuum distillation. 9.62 g (53%) 67, b.p. 103–105° C./0.7 mbar was obtained as a colourless liquid.

Analogously to example 9, 6.5 g colourless oil was obtained from 9.10 g (30.0 mmol) 67 and 4.64 g (36.0 mmol) dichloroacetic acid after flash chromatography (mobile solvent: petroleum ether/ethyl acetate 7:3 1% glacial acetic acid). Low-temperature crystallization from toluene yielded 4.88 g (46%) 15 of melting point 67–68° C.

Example 16

2,2-Dichloro-14-phenyl-tetradecanoic acid (16)

1-Bromo-12-phenyl-dodecane (68)

12.2 g (61%) 68 was obtained as a colourless liquid with a b.p. of 130–140° C./0.7 mbar from 19.7 g (60 mmol) 1,12-dibromodecane, 11.31 g (72.0 mmol) bromobenzene, 2.10 g magnesium and 10 ml (1 mmol) $Li_2CuCl_4$ (0.1 M in THF) in an analogous manner to the preparation of 67 (example 15). A solution of 9.94 g (30.0 mmol) 68 was added at –78° C. to an enolate solution prepared as in example 1 from 7.27 g (72.0 mmol) diisopropylamine, 29 ml (72.0 mmol) butyllithium (2.5 M in hexane) and 4.64 g (30.0 mmol) dichloroacetic acid in THF and allowed to slowly thaw in a cooling bath. After –30° C. had been reached it was again cooled to –50° C. and allowed to reach –20° C. After addition of 50 ml 3 N HCl and 200 ml ethyl acetate it was washed twice with 150 ml 3 N HCl each time and twice with saturated NaCl solution. After drying over sodium sulfate and removing the solvent on a rotary evaporator, it was purified by flash filtration on silica gel (mobile solvent: petroleum ether/ethyl acetate 7:3 1% glacial acetic acid). Saturated sodium bicarbonate solution was added to the solution obtained, the precipitated sodium salt was suction filtered, washed with petroleum ether and recrystallized twice from ethyl acetate. 6.72 g (56%) of the colourless sodium salt of 16 with a melting point of 171° C. (decomp.) was obtained.

Example 17

2,2-Dichloro-10-phenyl-decanoic acid (17)

1-Bromo-8-phenyl-octane (69)

12.2 g (61%) 69 was obtained as a colourless liquid with a b.p. of 110–120° C./0.7 mbar from 16.3 g (60 mmol)

1,8-dibromooctane, 11.31 g (72.0 mmol) bromobenzene, 2.10 g magnesium and 10 ml (1 mmol) $Li_2CuCl_4$ (0.1 M in THF) in an analogous manner to the preparation of 67 (example 15).

A solution of 9.94 g (30.0 mmol) 69 was added at −78° C. to an enolate solution prepared as in example 1 from 7.27 g (72.0 mmol) diisopropylamine, 29 ml (72.0 mmol) butyllithium (2.5 M in hexane) and 4.64 g (30.0 mmol) dichloroacetic acid in THF and allowed to slowly thaw in a cooling bath. After −30° C. had been reached it was again cooled to −50° C. and allowed to reach −20° C. After addition of 50 ml 3 N HCl and 200 ml ethyl acetate it was washed twice with 150 ml 3 N HCl each time and twice with saturated NaCl solution. After drying over sodium sulfate and removing the solvent on a rotary evaporator, it was purified by flash filtration on silica gel (mobile solvent: petroleum ether/ethyl acetate 7:3 1% glacial acetic acid). Saturated sodium bicarbonate solution was added to the solution obtained, the precipitated sodium salt was suction filtered, washed with petroleum ether and recrystallized twice from ethyl acetate. 3.5 g (35%) of the colourless sodium salt of 17 with a melting point of 154–156° C. was obtained.

Example 18

2,2-Dichloro-7-(4-chlorophenyl)-heptanoic acid (18)

5-(4-Chlorophenyl)-pentyl bromide (70)

15.7 g (53%) 70 was obtained as a colourless liquid with a b.p. of 115–117° C./0.05 mbar from 13.8 g (60 mmol) 1,5-dibromopentane, 13.8 g (72.0 mmol) 4-bromo-1-chlorobenzene, 1.95 g (80 mmol) magnesium and 10 ml (1 mmol) $Li_2CuCl_4$ (0.1 M in THF) in an analogous manner to the preparation of 67 (example 15).

4.7 g (79%) 18 was obtained as a colourless oil analogously to example 17 from 5.00 g (19.1 mmol) 70 and 9.81 g (76.4 mmol) dichloroacetic acid after flash chromatography (petroleum ether/ethyl acetate 10:1). The sodium salt of 18 was prepared analogously to example 17. 4.7 g (74%), melting point 158–162° C.

Example 19

2,2-Dichloro-12-(4-methylphenyl)-dodecanoic acid (19)

1-Bromo-10-(4-methylphenyl)-decane (71)

11.0 g (57%) 71 was obtained as a colourless liquid with a b.p. of 105–120° C10.7 mbar from 18.0 g (60 mmol) 1,10-dibromodecane, 12.3 g (72.0 mmol) 4-bromotoluene, 2.10 g (86.0 mmol) magnesium and 10 ml (1 mmol) $Li_2CuCl_4$ (0.1 M in THF) in an analogous manner to the preparation of 67 (example 15).

A solution of 9.94 g (30.0 mmol) 71 was added at −78° C. to an enolate solution prepared as in example 1 from 7.27 g (72.0 mmol) diisopropylamine, 29 ml (72.0 mmol) butyllithium (2.5 M in hexane) and 4.64 g (30.0 mmol) dichloroacetic acid in THF and allowed to slowly thaw in a cooling bath. After −30° C. had been reached it was again cooled to −50° C. and allowed to reach −20° C. After addition of 50 ml 3 N HCl and 200 ml ethyl acetate it was washed twice with 150 ml 3 N HCl each time and twice with saturated NaCl solution. After drying over sodium sulfate and removing the solvent on a rotary evaporator, it was purified by flash filtration on silica gel (mobile solvent: petroleum ether/ethyl acetate 7:3 1% glacial acetic acid). Saturated sodium bicarbonate solution was added to the solution obtained, the precipitated sodium salt was suction filtered, washed with petroleum ether and recrystallized twice from ethyl acetate. 5.87 g (52%) of the colourless sodium salt was obtained. The acid 19 was liberated by suspending the salt in ethyl acetate and acidifying with 3 N HCl. 4.5 g (40%) 19 of melting point 58–59° C. was obtained after drying the organic phase over sodium sulfate, evaporating the solvent in a vacuum and crystallizing from petroleum ether.

Example 20

2,2-Dichloro-12-(4-methoxyphenyl)-dodecanoic acid (20)

1-Bromo-10-(4-methoxyphenyl)-decane (72)

11.4 g (23%) 72 was obtained as a colourless liquid with a b.p. of 178–190° C./0.7 mbar from 60.0 g (0.200 mmol) 1,10-dibromodecane, 28.0 g (0.15 mol) 4-bromoanisole, 4.8 g (0.20 mol) magnesium and 20 ml (1 mmol) $Li_2CuCl_4$ (0.1 M in THF) in an analogous manner to the preparation of 67 (example 15). A total of 2.6 g (20%) of colourless compound 20, melting point 48–49° C. was obtained from 11.4 g (34.8 mmol) 72 and 5.15 g (40.0 mmol) dichloroacetic acid by the same method as in example 19.

Example 21

2,2-Dichloro-12-(4-chlorophenyl)-dodecanoic acid (21)

1-Bromo-10-(4-chlorophenyl)-decane (73)

20 ml (2.0 mmol) of a $Li_2CuCl_4$ solution (0.1 M in THF) was added to a solution of 40.0 g (130 mmol) 1,10-dibromodecane in 110 ml tetrahydrofuran and 100 ml of a 1 M 4-chlorophenylmagnesium bromide solution (Aldrich) in ether was added dropwise at room temperature within 4 hours. It was stirred for a further 18 hours, hydrolyzed with 100 ml 3 N HCl, diluted with 300 ml ethyl acetate, washed in each case with 300 ml 3 N HCl, saturated $NH_4Cl$ solution and NaCl solution, the organic phase was dried over sodium sulfate and concentrated on a rotary evaporator. The residue was fractionated in a vacuum. 8.0 g (24%) 73, b.p. 170–175° C./0.8 mbar.

Analogously to example 19, pale yellow 21 was obtained from 8.00 g (24.0 mmol) 73 and 6.45 g (50.0 mmol) dichloroacetic acid, it was colourless after crystallization from petroleum ether at −30° C., melting point <room temperature. In order to form the Na salt, the acid was dissolved in 100 ml ethyl acetate and admixed with saturated $NaHCO_3$ solution, the organic phase was washed twice with saturated NaCl solution and dried over sodium sulfate. Petroleum ether was added in such an amount that a slight turbidity started and it was allowed to stand overnight at room temperature. 2.4 g (30%) of the Na salt of 21 was obtained as colourless flakes, melting point°C.

Example 22

2,2-Dichloro-7-(5-pheylpentoxy)heptanoic acid (22)

1-Bromo-5-(5-phenylpentoxy)pentane (74)

2.40 g (14.6 mmol) 5-phenyl-1-pentanol was added dropwise to a suspension of 610 mg (15.0 mmol) sodium hydride (60% in white oil) in 5 ml THF. After the generation of hydrogen was completed, 9.6 ml (33 mmol) 1,5- dibromopentane was added and it was heated for 6 h to 80° C. After flash filtering the reaction mixture over silica gel (mobile solvent: petroleum ether) 8.3 g of a colourless liquid was obtained from which 3.50 g (76%) 64 was isolated as a colourless liquid by flash chromatography (petroleum ether).

3.03 g (9.67 mmol) 74 was reacted with 1.93 (15.0 mmol) dichloroacetic acid analogously to example 15. 2.5 g was obtained after flash chromatography (petroleum ether/ethyl acetate 9:1, 1% glacial acetic acid) which yielded 1.6 g pure 22 of melting point 83–84° C. after crystallization from toluene.

Example 23

2,2-Dichloro-14-phenyl-tetradec-13-ynoic acid (23)

1-Bromo-12-phenyl-dedec-11-yne (75)

37.2 ml (84.0 mmol) butyllithium (2.35 M in hexane) is added dropwise to a solution of 8.20 g (80.0 mmol) phenylacetylene in 70 ml THF which had been cooled to –78° C. and subsequently 50.42 g (168 mmol) 1,10-dibromodecane was added. It was allowed to reach room temperature and heated for 12 h to reflux. After addition of 80 ml semi-saturated ammonium chloride solution it was extracted with isohexane, dried over magnesium sulfate and concentrated by evaporation. The residue was fractionated by bulb tube distillation, 13.4 g (52%) 75, b.p. 95° C./0.05 mbar.

Analogously to example 17 6.70 g (20.9 mmol) 75 was reacted with 10.8 g (83.4 mmol) dichloroacetic acid. 2.3 g (30%) 23 was obtained which was converted into the sodium salt of 23, 1.2 g, melting point 155–157° C.

Example 24

2,2-Dichloro-14-phenylsulfenyl-tetradecanoic acid (24)

2,2-Dichloro-14-phenylsulfenyl-tetradecanoic acid ethyl ester (76)

3.46 g (25.0 mmol) potassium carbonate and 2.75 g (25.0 mmol) thiophenol were added to a solution of 10.1 g (25.0 mmol) 3 in 200 ml dimethylformamide. It was stirred for 12 h at room temperature, 300 ml water was added, it was extracted with ether, washed with water, dried over sodium sulfate and the solvent was removed on a rotary evaporator. 6.62 g (61%) 66 was obtained as a nearly colourless oil after flash chromatography of the residue (silica gel, heptane/toluene 5:1).

1.5 g (3.5 mmol) 76 was dissolved in 3.8 ml ethanol and admixed with 3.8 ml 1 N KOH. The precipitate that formed after a short time was dissolved in 20 ml ethanol/water 1:1. 1 ml 1 N KOH was added after 5 h and it was stirred for a further 6 h. After acidifying with 2 N HCl it was extracted with ether, dried over magnesium sulfate and the solvent was removed. 1.18 g (92%) 24 was obtained as colourless crystals of melting point 74° C.

Example 25

2,2-Dichloro-14-phenylsulfinyl-tetradecanoic acid (25)

2,2-Dichloro-14-phenylsulfinyl-tetradecanoic acid ethyl ester (27)

0.72 g (4.15 mmol, 0.96 g 75% acid) metachloroperbenzoic acid dissolved in 15 ml dichloromethane was added at 0 to –5° C. to a solution of 1.80 g (4.15 mmol) 66 in 30 ml dichloromethane. It was allowed to reach room temperature within 2 h and the organic phase was washed with sodium bicarbonate solution and water. After drying over magnesium sulfate and removing the solvent, it was purified by flash chromatography (heptane/ethyl acetate 2:1) 1.24 g (66%) 77 was obtained as a colourless oil.

0.46 g (1.02 mmol) 77 was stirred for 2 h at room temperature with 2.0 ml ethanol and 2.0 ml 1 N KOH and subsequently acidified with 2 N HCl. It was extracted with ether, washed with water, dried (sodium sulfate) and 0.41 g (95%) 25 was obtained after removing the solvent by evaporation as a colourless oil which crystallized after storage in a refrigerator, melting point 68° C.

Example 26

2,2-Dichloro-14-phenylsulfonyl-tetradecanoic acid (26)

2,2-Dichloro-14-phenylsulfonyl-tetradecanoic acid ethyl ester (78)

4.5 ml 30% hydrogen peroxide was added to a solution of 1.50 g (3.46 mmol) 76 in 15 ml glacial acetic acid, it was stirred for 48 h and ice water was added. After extracting with ether, drying (sodium sulfate) and removing the solvent, 1.23 g (77%) 78 was obtained as a colourless oil.

1.22 g (2.62 mmol) 78 was admixed with 5.2 ml ethanol and 5.2 ml 1 N KOH and stirred for 3 hours. It was cooled to 0° C. and acidified with 2 N HCl. The precipitated precipitate was suction filtered, washed with water and isohexane and dried in a vacuum. 1.12 g (97%) 26, colourless crystals, melting point 69–71° C.

Example 27

2,2-Dichloro-7-[5-(4-chlorophenyl)phenylsulfenyl]-heptanoic acid (27)

5-(4-chlorophenyl)-1-pentanethiol (79)

24.2 g (92.6 mmol) 5-(4-chlorophenyl)-pentyl bromide 60 in 60 ml ethanol was added to a solution of 10.6 g (0.139 mmol) thiourea in 40 ml ethanol. It was heated for 5 h to reflux, allowed to cool, admixed with 50 ml concentrated ammonia solution and again heated for 3 h to reflux. After cooling it was acidified to pH 1 with ca. 30 ml concentrated HCl and extracted twice with 150 ml ether. It was washed with saturated NaCl solution, dried over sodium sulfate and the solvent was removed on a rotary evaporator, 19.0 g (95%) 79 was obtained. A mixture of 5.00 g (16.3 mmol) 79, 2.25 g (16.3 mmol) potassium carbonate, 3.50 g (16.3 mmol) 6 and 50 ml dimethylformamide was stirred for 12 h at room temperature. It was admixed with water and extracted with ether. The ether phase was washed with water, dried over sodium sulfate and concentrated by evaporation. 7.1 g yellow oil which yielded 5.06 g (71%) of the ethyl ester of 27 after flash chromatography (toluene/heptane 1:2).

A mixture of 1.50 g (3.41 mmol) of the ester obtained, 6.82 ml (6.82 mmol) 1 N KOH and 7 ml ethanol was stirred for 3 h at room temperature. After acidifying with 2 N HCl and extracting with ether it was washed with water and dried (Na$_2$SO$_4$). After removing the solvent, 1.21 g (86%) 27 remained as a colourless oil. The sodium salt was prepared from 1.13 g 27 and 110 mg sodium hydroxide and washed with ether. 0.75 g (64%), melting point 155–157° C.

Example 28

2,2-Dichloro-14-(4-isopropylphenoxy)-tetradecanoic acid (28)

1-Bromo-12-(4-isopropylphenoxy)-dodecane (80)

10.0 g (41%) 70 of melting point 51–52° C. (ether) was obtained analogously to the preparation of 62 (example 10)

after flash chromatography (ethyl acetate/heptane 1:10) from 8.85 g (65.0 mmol) 4-isopropylphenol, 1.60 g (65 mmol) sodium hydride and 23.0 g (70.0 mmol) 1,12-dibromododecane.

4.00 g (10.0 mmol) 80 was reacted with 5.16 g (40.0 mmol) dichloroacetic acid as in example 9. Yield 0.9 g (21%) 28, melting point 47–49° C. The sodium salt obtained from 28 and sodium hydroxide in ethanol melted at 109° C. (decomp.).

Example 29

2,2-Dichloro-12-(2,6-diisopropylphenoxy)-dodecanoic acid (29)

1-Bromo-10-(2,6-diisopropylphenoxy)-decane (81)

13.95 g (54%) 81 was obtained analogously to the preparation of 62 (example 10) as a light-yellow oil after flash chromatography (ethyl acetate/heptane 1:10) from 11.6 g (65.0 mmol) 2,6-diisopropylphenol, 1.60 g (65.0 mmol) sodium hydride and 21.0 g (70.0 mmol) 1,10-dibromodecane.

7.95 g (20.0 mmol) 81 was reacted with 10.3 g (80.0 mmol) dichloroacetic acid as in example 9. Flash chromatography (ethyl acetate/heptane 1:10) yielded 4.7 g (53%) 29 as a light coloured oil.

Example 30

2,2-Dichloro-14-[4-(4-chlorophenylcarbonylamino)-phenylsulfenyl]-tetradecanoic acid (30)

2,2-Dichloro-14-[4-(4-chlorophenylcarbonylamino)-phenylsulfenyl]-tetradecanoic acid ethyl ester (82)

390 mg (2.83 mmol) potassium carbonate and 1.14 g (2.83 mmol) 3 were added to a solution of 700 mg (2.83 mmol) 4-(4-chlorobenzoylamino)-thiophenol in 10 ml dimethylformamide and it was stirred for 50 h at room temperature. It was admixed with 20 ml water while cooling, the precipitate was suction filtered, washed with isohexane and dried in a vacuum. The 1.3 g (78%) crude product obtained was purified by flash chromatography (toluene). Yield 0.82 g (50%) 82, melting point 130–131° C. (dichloromethane/isohexane).

0.68 g (1.16 mmol) 82, 2.3 ml 1 N KOH and 8 ml ethanol were stirred for 2 h at room temperature. It was acidified with 2 N HCl in the cold, diluted with water, extracted with ether, washed with water, dried ($Na_2SO_4$) and the solvent was removed. Yield 0.61 g (98%) 30. It was dissolved in 1 ml ethanol and 44 mg NaOH in 0.5 ml ethanol was added in the cold. After precipitating by addition of ether, suction filtering and washing with ether, 0.46 g (61%) of the sodium salt of 30 with a melting point of 167–168° C. was obtained.

Example 31

2,2-Dichloro-12-(2-naphthyl)-dodecanoic acid (31)

1-Bromo-10-(2-naphthyl)-decane (83)

3.7 g (20%) 83 was obtained analogously to the preparation of 67 (example 15) as a pale yellow oil after flash chromatography (ethyl acetate/heptane 1:10) from 16.5 g (55.0 mmol) 1,10-dibromodecane, 13.3 g (64.2 mmol) 2-bromonaphthalene, 1.7 g (70 mmol) magnesium and 10 ml (1 mmol) $Li_2CuCl_4$ (0.1 M in THF).

3.1 g (79%) 31 of melting point 66–67° C. (ether) was obtained from 3.5 g (10.0 mmol) 83 and 5.16 g (40.0 mmol) dichloroacetic acid as in example 9.

Example 32

2,2-Dichloro-12-(4-methylsulfenylphenyl)-dodecanoic acid (32)

1-Bromo-10-(4-methylsulfenylphenyl)-decane (84)

11.2 g (59%) 84 was obtained analogously to the preparation of 67 (example 15) as a wax-like mass after flash chromatography (gradient elution, heptane →heptane/ethyl acetate 10:1) from 16.5 g (55.0 mmol) 1,10-dibromodecane, 13.1 g (64.2 mmol) 4-bromothio-anisole, 1.7 g (70.0 mmol) magnesium and 10 ml (1.0 mmol) $Li_2CuCl_4$ (0.1 M in THF).

1.1 g (14%) 32 was obtained as a colourless oil after flash chromatography (heptane/ethyl acetate 10:1→heptane/ethyl acetate 3:1) from 6.9 g (20.0 mmol) 84 and 10.32 g (80.0 mmol) dichloroacetic acid as in example 9. The sodium salt of 32 which was prepared analogously to example 30 exhibits decomposition at 143° C.

Example 33

2,2-Dichloro-7-[4-(4-chlorophenylcarbonylamino)phenyl-sulfenyl]-heptanoic acid (33)

2,2-Dichloro-7-[4-(4-chlorophenylcarbonylamino)phenyl-sulfenyl]-heptanoic acid ethyl ester (85)

1.14 g (63%) 85 of melting point 136–137° C. (ethyl acetate/isohexane) was obtained analogously to the preparation of 82 (example 30) after flash chromatography (toluene) from 940 mg (3.79 mmol) 4-(4-chlorobenzoyl-amino)-thiophenol, 10 ml dimethylformamide, 520 mg (3.79 mmol) potassium carbonate and 1.60 g (3.79 mmol) 6. 0.25 g (57%) 33 of melting point 140–142° C. was obtained by saponification (example 30) of 0.41 g (0.96 mmol) 85.

Example 34

2,2-Dichloro-8-[5-(4-chlorophenyl)pentylsulfenyl]-octanoic acid (34)

3.50 g (16.3 mmol) 89 was reacted analogously to example 27 with 5.2 g (16.3 mmol) of the ethyl ester of 7. 5.2 g (70%) 2,2-dichloro-8-[5-(4-chlorophenyl)-pentyl-sulfenyl]-octanoic acid ethyl ester 86 was obtained as a colourless oil after flash chromatography (heptanel toluene 2:1). 2.5 g (5.5 mmol) 86, 11 ml (11 mmol) 1 N KOH and 11 ml ethanol were stirred for 2 h at room temperature. It was acidified with 2 N HCl to pH 2 while cooling in an ice-bath, ethanol was removed by distillation, it was extracted with ether, washed with water, dried over $Na_2SO_4$ and, after removing the solvent, 2.24 g (96%) 34 was obtained as a colourless oil. 1.14 g (78%) of the sodium salt of 34 with a melting point of 154° C. was obtained from 1.41 g (3.29 mmol) 34 in 3 ml ethanol and 0.13 g (3.3 mmol) sodium hydroxide in 5 ml ethanol after mixing, admixing with ether, suction filtering and drying.

Example 35

12-Carbamoyl-2,2-dichloro-dodecanoic acid (35)

200 mg (0.70 mmol) 8 was fed into 10 ml 80% sulfuric acid and kept at room temperature for 6 h. The solution that was obtained was poured into 150 ml ice water, the beige-coloured precipitate was suction filtered and washed with petroleum ether. 180 mg (85%) 35, melting point 93–94° C.

Example 36

2,2-Dichloro-12-(4-methylsulfinylphenyl)-dodecanoic acid (32)

391 mg (1.00 mmol) 32 was dissolved in 10 ml dichloromethane and admixed at −5 to 0° C. with a solution of 173 mg (1.00 mmol) m-chloroperbenzoic acid in 10 ml dichloromethane. It was allowed to reach room temperature, stirred for a further 2 hours and the mixture was diluted with ice-water. It was extracted with dichloromethane, dried over $Na_2SO_4$, treated with active charcoal and concentrated by evaporation. The 0.5 g crude product obtained was purified by flash chromatography (toluene/dioxane/glacial acetic acid 15:12:1) and 0.20 g (50%) 36 with a melting point of 75–76° C. was obtained.

Example 37

2,2-Dichloro-7-[5-(4-chlorophenyl)pentylsulfinyl]-heptanoic acid (37)

2,2-Dichloro-7-[5-(4-chlorophenyl)pentylsulfinyl]-heptanoic acid ethyl ester (87)

1.60 g (3.64 mmol) 2,2-dichloro-7-[5-(4-chlorophenyl)-pentylsulfenyl]-heptanoic acid ethyl ester (example 27) was dissolved in 30 ml dichloromethane and a solution of 0.63 g (3.64 mmol) m-chloroperbenzoic acid in 15 ml dichloromethane was added dropwise at −5° C. It was stirred for 2 h at 0° C., the precipitated 3-chlorobenzoic acid was aspirated, it was washed twice with sodium bicarbonate solution, twice with water, dried over magnesium sulfate, concentrated in a vacuum and purified by flash chromatography (heptane/ethyl acetate 2:1). 1.2 g (73%) 87 as a colourless oil.

1.00 g (2.20 mmol) 87 was admixed with 4.4 ml (4.4 mmol) 1 N KOH and 4.4 ml ethanol. It was stirred for 4 h at room temperature, acidified in the cold to pH 2. During this the acid precipitated as a colourless finely crystalline precipitate which was suction filtered after stirring for 10 minutes and washed with isohexane/ether 10:1 and dried in a vacuum. 0.86 g (92%) 37, melting point 84–85° C.

Example 38

2,2-Dichloro-14-(4-chlorophenyl)-tetradec-8-ynoic acid (38)

4.5 g (12.4 mmol) 7-(4-chlorophenyl-1-hept-1-yne 88 was dissolved in a mixture of 100 ml dioxane and 40 ml toluene, cooled to −10° C., admixed with 5.1 ml (12.5 mmol) butyllithium (2.46 M in hexane) and subsequently with 9.7 g (25 mmol) 1,5-dibromopentane. It was heated for 14 h to 80° C., subsequently for 9 h to 100° C. and allowed to cool. It was admixed with 3 N HCl and extracted with isohexane. The organic phase was washed with water, dried over magnesium sulfate, concentrated and the residue is distilled in a bulb tube. 3.95 g 1-bromo-12-(4-chlorophenyl)-dodec-6-yne 89, b.p. 120° C./0.2 mbar.

3.90 g (11.1 mmol) 1-bromo-12-(4-chlorophenyl)-dodec-6-yne 89 was reacted with 11.4 g (89 mmol) dichloro-acetic acid analogously to example 9. 2.00 g (45%) 38 was obtained as a colourless oil.

Example 39

2,2-Dichloro-14-(4-tert.butylphenyl)-tetradecanoic acid (39)

1-Bromo-12-(4-tert.butylphenyl)-dodecane (90)

4.3 g (21%) 80 was obtained analogously to the preparation of 57 (example 15) as a pale yellow oil (boiling point 126–128° C./0.2 mbar) after flash chromatography (ethyl acetate/heptane 1:10) from 18.0 g (55 mmol) 1,12-dibromododecane, 13.7 g (64.2 mmol) 4-tert.butylbromobenzene, 1.7 g (70 mmol) magnesium and 10 ml (1 mmol) $Li_2CuCl_4$ (0.1 M in THF).

1.5 g (35%) 39 was obtained with a melting point of 47–48° C. from 3.9 g (10.2 mmol) 80 and 3.87 g (30 mmol) dichloroacetic acid as in example 9. The sodium salt was obtained analogously to example 30. Decomposition >174° C.

Example 40

2,2-Dichloro-12-(4-tert.butylphenyl)-dodecanoic acid (40)

1-Bromo-10-(4-tert.butylphenyl)-decane (91)

4.6 g (24%) 91 was obtained analogously to the preparation of 67 (example 15) as a pale yellow oil (boiling point 134° C./0.2 mbar) after flash chromatography (ethyl acetate/heptane 1:10) from 16.5 g (55 mmol) 1,10-dibromododecane, 13.7 g (64.2 mmol) 4-tert.butylbromobenzene, 1.7 g (70 mmol) magnesium and 10 ml (1 mmol) $Li_2CuCl_4$ (0.1 M in THF).

1.1 g (22%) 40 was obtained with a melting point of 46–48° C. from 4.6 g (13.0 mmol) 91 and 6.7 g (52.0 mmol) dichloroacetic acid as in example 9. The sodium salt was prepared analogously to example 30. Decomposition >176° C.

Example 41

2,2-Dichloro-12-(4-tert.butylphenoxy)-dodecanoic acid (41)

1-Bromo-10-(4-tert.butylphenoxy)-decane (92)

16.1 g (67%) 92 was obtained analogously to the preparation of 62 as a yellow oil from 9.75 g (65.0 mmol) 4-tert.butylphenol, 1.60 g (65 mmol) sodium hydride and 21.0 g (70.0 mmol) 1,10-dibromodecane after distillation at 170–175° C./0.06 mbar.

6.8 g (20 mmol) 92 was reacted with 10.3 g (80 mmol) dichloroacetic acid as in example 9. 2.8 g (35%) 41 with a melting point of 56–57° C. was obtained. The sodium salt obtained from 41 and pulverized NaOH in ethanol melted at 178° C. (decomp.).

Example 42

2,2-Dichloro-15-phenyl-pentadecanoic acid (42)

1-Bromo-13-phenyl-tridecane (93)

4.9 g (51%) 93 was obtained analogously to the preparation of 67 (example 15) as a colourless oil of melting point 158–159° C./0.15 mbar after distillation in a high vacuum from 7.48 g (27.5 mmol) dibromooctane, 7.27 g (32.1 mmol) 1-bromo-5-phenylpentane, 0.85 g (35 mmol) magnesium and 5 ml (0.5 mmol) $Li_2CuCl_4$ (0.1 M in THF).

1.3 g (67%) 42 was obtained with a melting point of 52–53° C. from 1.7 g (5 mmol) 93 and 2.58 g (20 mmol) dichloroacetic acid as in example 9. The sodium salt was prepared from 0.8 g (2.1 mmol) 42 using 84 mg (2.1 mmol) NaOH powder. 0.7 g melting point 170° C. (decomp.)

Example 43

2,2-Dichloro-13-phenyl-tridecanoic acid (43)

1-Bromo-11-phenyl-undecane (94)

7.5 g (44%) 94 was obtained analogously to the preparation of 67 (example 15) as a colourless oil with a boiling point of 150–152° C./0.4 mbar from 12.65 g (55 mmol) dibromopentane, 15.5 g (64.2 mmol) 1-bromo-6-phenylhexane, 1.7 g (70 mmol) magnesium and 10 ml (1 mmol) cuprate solution after distillation in a high vacuum.

5.1 g (71%) 43 was obtained from 6.23 g (20 mmol) 94 and 10.3 g (80 mmol) dichloroacetic acid as in example 9. Melting point 46–47° C.

The sodium salt obtained from 43 and pulverized NaOH in ethanol melted at 165° C. (decomp.).

Example 44

2,2-Dichloro-16-phenyl-hexadecanoic acid (44)

1-Bromo-14-phenyl-tetradecane (95)

8.7 g (45%) 95 was obtained analogously to the preparation of 67 (example 15) as a colourless oil with a boiling point of 168° C./0.15 mbar from 14.96 g (55 mmol) dibromooctane, 15.5 g (64.2 mmol) 1-bromo-6-phenyl-hexane, 1.7 g (70 mmol) magnesium and 10 ml cuprate solution after distillation.

1.55 g (20%) 44 was obtained with a melting point of 58–59° C. from 7.1 g (20 mmol) 95 and 10.3 g (80 mmol) dichloroacetic acid as in example 9. The sodium salt obtained from 44 and pulverized NaOH in ethanol melted at 166° C. (decomp.).

Example 45

2,2-Dichloro-14-cyclohexyl-tetradecanoic acid (45)

1-Bromo-12-cyclohexyl-dodecane (96)

10.6 g (49%) 96 was obtained analogously to the preparation of 67 (example 15) as a colourless oil from 15.86 g (65 mmol) dibromohexane, 19.8 g (80 mmol) 1-bromo-6-cyclohexyl-hexane, 2.42 g (0.1 mmol) magnesium and 10 ml cuprate solution after flash chromatography on silica gel (mobile solvent: heptane, heptane/ethyl acetate 10:1).

1.65 g (20%) 45 was obtained with a melting point of 68–69° C. from 7.5 g (22.63 mmol) 96 and 8.75 g (67.89 mmol) dichloroacetic acid analogously to example 5. The sodium salt obtained from 45 and pulverized NaOH in ethanol melted at 146–148° C.

Example 46

2,2-Dichloro-13-cyclohexyl-tridecanoic acid (46)

1-Bromo-11-cyclohexylundecane (97)

6.81 g (43%) 97 was obtained analogously to the preparation of 67 (example 15) after distillation as a colourless oil with a boiling point of 106–110° C./0.006 mbar from 17.6 g (75 mmol) 1,6-dibromohexane, 11.66 g (50 mmol) 1-bromo-5-cyclohexylpentane, 1.46 g (60 mmol) magnesium and 10 ml cuprate solution.

2.16 g (62%) 46 with a melting point of 50–51° C. was obtained from 3.0 g (9.45 mmol) 97 and 3.66 g (28.36 mmol) dichloroacetic acid analogously to example 5. The sodium salt obtained from 46 and pulverized NaOH in ethanol melted at 166–168° C. (decomp.).

Example 47

2,2-Dichloro-15-cyclohexyl-pentadecanoic acid (47)

1-Bromo-13-cyclohexyl-tridecane (98)

8.14 g (47%) 98 was obtained analogously to the preparation of 57 (example 15) after distillation as a colourless oil with a boiling point of 121–125° C./0.005 mbar from 20.4 g (75 mmol) 1,8-dibromooctane, 11.66 g (50 mmol) 1-bromo-5-cyclohexylpentane, 1.46 g (60 mmol) magnesium and 10 ml cuprate solution.

1.0 g (21%) 47 with a melting point of 53–56° C. was obtained from 4.2 g (12.24 mmol) 98 and 4.74 g (36.72 mmol) dichloroacetic acid analogously to example 5. The sodium salt obtained from 47 and pulverized NaOH in ethanol melted at 162–164° C.

Example 48

2,2-Dichloro-16-cyclohexyl-hexadecanoic acid (48)

1-Bromo-14-cyclohexyl-tetradecane (99)

4.5 g (53%) 99 was obtained analogously to the preparation of 67 (example 15) after distillation from 10.87 g (38 mmol), 1,9-dibromononane, 5.6 g (24 mmol) 1-bromo-5-cyclohexyl-pentane, 0.73 g (30 mmol) magnesium and 5 ml cuprate solution.

3.53 g (73%) 48 with a melting point of 72–73° C. was obtained from 4.4 g (12.24 mmol) 99 and 4.74 g (36.72 mmol) dichloroacetic acid analogously to example 5. The sodium salt prepared from 48 and pulverized NaOH in ethanol melted at 156–158° C.

Example 49

2,2-Dichloro-17-cyclohexyl-heptadecanoic acid (49)

1-Bromo-15-cyclohexyl-pentadecane (100)

24.1 g (86%) 100 was obtained analogously to the preparation of 67 (example 15) after distillation from 22.51 g (75 mmol) 1,10-dibromodecane, 11.7 g (40 mmol) 1-bromo-5-cyclohexylpentane, 1.21 g (50 mmol) magnesium and 5 ml cuprate solution.

1.84 g (25%) 49 of melting point 65–66° C. was obtained from 6.5 g (17.4 mmol) 100 and 6.73 g (52.21 mmol) dichloroacetic acid analogously to example 5. The sodium salt prepared from 49 and pulverized NaOH in ethanol melted at 152–155° C. (decomp.).

Example 50

2,2-Dichloro-14-(4-chlorophenyl-tetradecanoic acid (50)

1-Bromo-6-(4-chlorophenyl)-hexane (101)

20.5 g (47%) 101 with a boiling point of 158–162° C./3.5 mbar was obtained analogously to the preparation of 67 (example 15) after distillation over a Vigreux column from 50 ml (330 mmol) 1,6-dibromohexane, 30 g (160 mmol) 101, 4-chlorobromobenzene, 3.8 g (160 mmol) magnesium and 20 ml cuprate solution.

1-Bromo-12-(4-chlorophenyl)-dodecane (102)

18.5 g (71%) 102 was obtained analogously to the preparation of 67 (example 15) after flash chromatography on silica gel from 25 ml (140 mmol) 1,6-dibromohexane, 20 g (72 mmol) 101, 1.8 g (72 mmol) magnesium and 20 ml cuprate solution.

8.6 g (70%) 50 was obtained from 10.8 g (30 mmol) 102 and 6.45 g (50 mmol) dichloroacetic acid analogously to example 5. The sodium salt prepared from 50 and pulverized NaOH in ethanol melted at 163–164° C.

Example 51

2,2-Dichloro-12-(4-methylsulfonyl-phenyl-dodecanoic acid (51)

4.0 g (10.2 mmol) 32 and 3.4 ml 30% hydrogen peroxide in 10 ml glacial acetic acid were heated to 90° C. for 1 hour and poured into ice water. After extracting with ether, drying (sodium sulfate) and removing the solvent, 3.8 g (84%) 51 of melting point 167–168° C. was obtained.

Example 52

2,2-Dichloro-hexadecanoic acid (52)

2.45 g (38%) 52 of melting point 34–37° C. was obtained from 5.55 g (20 mmol) 1-tetradecyl bromide (Aldrich) and 7.74 g (60 mmol) dichloroacetic acid analogously to example 5. The sodium salt prepared from 52 and pulverized NaOH in ethanol melted at 165–168° C.

Example 53

2,2-Dichloro-eicosanoic acid (53)

10.4 g (82%) 53 of melting point 49–51° C. was obtained from 11.1 g (33.34 mmol) 1-octadecyl bromide (Aldrich) and 12.89 g (0.1 mmol) dichloroacetic acid analogously to example 5. The sodium salt prepared from 53 and pulverized NaOH in ethanol melted at 147–149° C.

Example 54

2,2-Dichloro-12-(4-chlorophenyl-sulfenyl)-dodecanoic acid (54) 12-Bromo-2,2-dichloro-dodecanoic acid ethyl ester (103)

10.0 g (28.7 mmol) 1 was reacted with 4.19 g (33 mmol) oxalyl chloride, 3.04 g (66 mmol) ethanol and 6.67 g (66 mmol) triethylamine to form 9.9 g (92%) 103 as a colourless oil analogously to example 3.

2,2-Dichloro-12-(4-chlorophenylsulfenyl)-dodecanoic acid ethyl ester (104)

5.24 g (94%) 104 was obtained as a pale yellow oil from 1.85 g (12.76 mmol) 4-chlorothiophenol, 100 ml DMF, 1.76 g (12.76 mmol) potassium carbonate and 4.8 g (12.76 mmol) 103 analogously to example 30 (preparation of 82).

1.29 g (84%) 54 with a melting point of 74–78° C. was obtained by saponification (example 30) of 1.65 g (3.73 mmol) 104.

The sodium salt prepared from 54 and pulverized NaOH in ethanol melted at 154–157° C.

Example 55

2,2-Dichloro-12-(4-chlorophenyl-sulfinyl)-dodecanoic acid (55)

2,2-Dichloro-12-(4-chlorophenyl-sulfinyl)-dodecanoic acid ethyl ester (105)

0.59 g (3.41 mmol) chloroperbenzoic acid dissolved in 15 ml dichloromethane was added dropwise to a solution of 1.5 g (3.41 mmol) 104 in 30 ml dichloromethane analogously to example 25 (preparation of 77). 1.24 g (80%) 105 was obtained after flash chromatography on silica gel. 1.24 g (2.72 mmol) 105 was admixed with 5.5 ml ethanol and 5.5 ml 1 N KOH and cooled for 5 hours at room temperature. It was cooled to 0° C. and acidified with 2 N HCl. The precipitated precipitate was suction filtered, washed with water and isohexane and dried in a vacuum, yield: 0.65 g (56%) 55. The sodium salt prepared from 55 and pulverized NaOH in ethanol melted at 91–94° C.

Example 56

2,2-Dichloro-12-(4-chlorophenyl-sulfinyl)-dodecanoic acid (56)

2,2-Dichloro-12-(4-chlorophenyl-sulfinyl)-dodecanoic acid ethyl ester (106)

2.0 g (4.55 mmol) 104 and 6 ml 30% hydrogen peroxide in 20 ml glacial acetic acid were oxidized to form 2.08 g (99%) 106 as a colourless oil analogously to 78 (example 26).

1.8 g (96%) 56 with a melting point of 84° C. was obtained by saponification (example 26) from 2 g (4.24 mmol) 96 and 8.5 ml (8.48 mmol) 1 N KOH. The sodium salt prepared from 56 and pulverized NaOH in ethanol melted at 144–147° C.

Example 57

2,2-Dichloro-14-phenyl-tetradecanoic acid methyl ester (57)

1.98 g (5 mmol) 16 was stirred for 2 hours at 40° C. with 1.27 g (10 mmol) oxalyl chloride in 20 ml absolute methanol analogously to 103 (example 54). 1.1 g (57) 57 was obtained.

Example 58

2,2-Dichloro-13-(cyclohexyl-oxy)-tridecanoic acid (58)

1-Bromo-11-(cyclohexyl-oxy)-undecane (107)

5.6 g (58%) 107 was obtained as a pale yellow oil from 1.22 g (30 mmol) sodium hydride (60% in white oil) and 2.92 g (29.2 mmol) cyclohexanol and 18.85 g (60 mmol) 1,11-dibromoundecane (Aldrich) analogously to 74 (example 22).

1.25 g (21%) 58 was obtained as a colourless oil after flash chromatography on silica gel from 5.41 g (16.23 mmol) 107 and 6.28 g (48.96 mmol) dichloroacetic acid analogously to example 9.

The sodium salt obtained from 58 and pulverized NaOH in ethanol melted at 75–78° C.

Example 59

2,2-Dichloro-14-(4-chlorophenyl-sulfonylamino)-tetradecanoic acid (59)

11-cyano-undecanol-(1) (108)

7.89 (0.12 mol) potassium cyanide dissolved in 20 ml water was added dropwise at 100° C. within 1 hour to a solution of 25.1 g (0.1 mol) 11-bromoundecanol-(1) in 50 ml DMSO. After stirring for 6 hours under reflux it was cooled, diluted with 100 ml water and extracted from ether. After washing the organic phase it was dried (MgSO$_4$) and concentrated. 11.1 g (53%) colourless crystals of melting point 34–35° C. were obtained after flash chromatography on silica gel (heptane/ethyl acetate 5:1).

12-Amino-dodecanol-(1) (109)

11.0 g (52 mmol) 108 in 150 ml methanol containing 5.0 g Raney-Nickel catalyst was hydrogenated with hydrogen for 8 hours at 80° C./120 bar with addition of 50 ml liquid ammonia in a high-pressure hydrogenation instrument. 10.3 g (98%) 109 was obtained as a pale yellow oil after filtration, concentration and blow-off.

12-(4-chlorophenyl-sulfonylamino)-dodecanol-(1) (110)

10 g (46.4 mmol) 109 was dissolved in 200 ml pyridine and 9.8 g (46.4 mmol) p-chlorobenzenesulfonic acid chloride was added at 30° C. It was stirred overnight at room temperature, the main portion of pyridine was removed by distillation and the residue was dispersed between water and ether. 5.9 g (34%) 110 with a melting point of 90–92° C. was obtained after concentrating the organic phase.

1-Bromo-12-(4-chlorophenyl-sulfonylamino)-dodecane (111)

5.62 (15 mmol) 110 was heated for 2 hours at 40° C. with 15 ml phosphorus tribromide, cooled, poured into ice water and extracted with ether. After drying (MgSO$_4$) and concentrating, 5.16 g (78%) 111 with a melting point of 70–73° C. was obtained. 0.6 g (46%) 59 was obtained as a colourless crystallisate with a flash point of 70° C. after flash chromatography on silica gel from 1.3 g (3 mmol) 111 and 2.3 g (18 mmol) dichloroacetic acid as in example 9. The sodium salt obtained from 59 and pulverized NaOH in ethanol melted at 150–152° C.

Example 60

Pharmacological Test Report

Rat hepatic cells in culture are suitable for investigations on cellular metabolism. These primary cultures have the advantage that several substances can be examined comparatively in a non-proliferating system i.e. in a system which is primarily controlled by metabolic processes.

Hepatic cells from the rat were isolated by recirculating collagenase perfusion and cultured in slanted bottom tubes. The insulin-stimulated incorporation of $^{14}$C acetate into triglycerides (TG) was examined in the presence and absence of test substances.

TABLE

Effect of 2,2-dichloroalkanecarboxylic acids on the incorporation of $^{14}$C acetate into triglycerides (TG) in prirnary monolayer cultures of liver cells from male Sprague-Dawley rats during an incubation period of 48 hours in serum-free Dulbecco MEM. The differences to controls treated with solvent (DMSO 0.1% v/v) is given in percent (4 culture plates of 2 preparations).

| Substances (compound of the examples) | % Increase in the incorporation of $^{14}$C into $^{14}$C TG |
|---|---|
| Example 10 | 23 |
| Example 32 | 51 |
| Example 9 | 31 |
| Example 11 | 28 |
| Example 16 | 36 |
| Example 46 | 28 |
| Example 47 | 19 |

The 2,2-dichloroalkanecarboxylic acids mentioned here lead to a significant increase in the insulin-stimulated incorporation of $^{14}$C acetate into triglycerides. This indicates that the compounds according to the invention have an antidiabetic effect. This effect is manifested in particular by a strong reduction of the TG de novo synthesis.

We claim:

1. A method of treating diabetus mellitus in a patient in need of such treatment, comprising administering an antidiabetic amount of a compound of formula (I) to said patient:

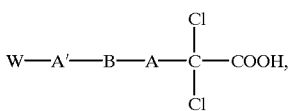

wherein

A is an alkylene chain of 5–20 carbon atoms;

A' is a valency bond, a vinylene or acetylene group or an alkylene chain of 1–10 carbon atoms;

B is a valency bond, a methylene group, a sulfoxide group, sulphur, oxygen or a NR$^1$ group, wherein R$^1$ is hydrogen, benzyl, phenyl or a C$_1$–C$_4$ alkyl residue, or B is a carbonyl, sulfonamide, sulfoxide or sulfone group, an E- or Z-vinylene or an acetylene group, a CR$^2$R$^3$ group wherein R$^2$ is hydrogen, a C$_1$–C$_4$ alkyl residue or phenyl, and R$^3$ is a C$_1$–C$_4$ alkyl residue, benzyl, phenyl, hydroxy or a group NR$^4$R$^5$, wherein R$^4$ is hydrogen, benzyl, phenyl or a C$_1$–C$_4$ alkyl residue and R$^5$ is hydrogen or a C$_1$–C$_4$ alkyl residue, or B is a group Y—Z—Y, wherein Y is sulphur or oxygen, and Z is an alkyl chain (CH$_2$)$_n$, wherein n is 1–5; and W is a halogen atom; a cyano or thiocyano group; an aminocarbonyl group, a methyl, isopropyl or t-butyl residue; a C$_3$–C$_8$ cycloalkyl residue which is unsubstituted or substituted by phenyl or C$_1$–C$_4$alkyl; a cyclohexenyl or cyclopentenyl residue; a phenyl ring which is unsubstituted or substituted by at least one of C$_1$–C$_4$ alkyl, C$_1$–C$_4$ alkoxy, C$_1$–C$_4$ alkylthio, C$_1$–C$_4$ alkylsulfinyl, C$_1$–C$_4$ alkylsulfonyl, trifluoromethyl, nitro, amino, hydroxy, cyano, mercapto, carboxy, phenoxy, benzyloxy, phenyl, benzol, carboxy-C$_1$–C$_4$-alkyl, methylenedioxy, ethylenedioxy, fluorine, chlorine, bromine, iodine, carboxymethoxy, caboxyethoxy, acetoxy, acetyl, propionyl, a NR$^6$R$^7$ group, wherein R$^6$ is hydrogen, C$_1$–C$_4$ alkyl or benzyl and R$^7$ is hydrogen, C$_1$–C$_4$ alkyl, benzyl, phenyl or benzoyl; wherein an aromatic ring of R$^6$ or R$^7$ is unsubstituted or substituted by at least one of halogen, hydroxy or C$_1$–C$_4$ alkoxy, or R$^7$ is an α- or β-naphthyl ring which is unsubstituted or substituted by at least one of methyl, hydroxy, methoxy, carboxy, methoxycarbonyl, ethoxycarbonyl, cyano, acetyl, chlorine or bromine or a tetrahydronaphthyl residue;

or a physiologically tolerated salt or ester or optical isomer thereof.

2. The method of claim 1, wherein

A is an alkylene claim of 8–14 carbon atoms;

A' is a valency bond, or a vinylene or acetylene group;

B is a valency bond, oxygen, a methylene group, sulfur, or a sulfoxide or sulfonyl group; and W is a C$_3$–C$_8$ cycloalkyl residue or a substituted or unsubstituted phenyl residue.

3. The method of claim 2, wherein A is an alkylene claim of 10–12 carbon atoms.

4. The method of claim 2, wherein W is 4-chlorphenyl, 4-methylthiophenyl, 4-C$_1$–C$_4$-alkylphenyl or 4-methylsulfonylphenyl.

5. A compound of the formula

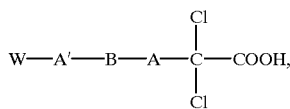
(I)

wherein
- A is an alkylene chain of 5–20 carbon atoms;
- A' is a valency bond, a vinylene or acetylene group or an alkylene chain of 1–10 carbon atoms;
- B is a valency bond, a methylene group, sulphur, oxygen or a group $-NR^1-$, wherein $R^1$ is hydrogen, benzyl, phenyl or a $C_1-C_4$ alkyl residue,
  or B is a carbonyl, sulfonamide, sulfoxide or sulfone group, an E- or Z-vinylene or an acetylene group, a $CR^2R^3$ group, wherein $R^2$ is hydrogen, a $C_1-C_4$ alkyl residue or phenyl, and $R^3$ is a $C_1-C_4$ alkyl residue, benzyl, phenyl, hydroxy or a group $-NR^4-R^5$, wherein $R^4$ is hydrogen, benzyl, phenyl or a $C_1-C_4$ alkyl residue and $R^5$ is hydrogen or a $C_1-C_4$ alkyl residue, or B is a group Y—Z—Y, wherein Y is sulphur or oxygen and Z is an alkyl chain $(CH_2)_n$ wherein n is 1–5; and
- W is a $C_3-C_8$ cycloalkyl residue which is unsubstituted or substituted by phenyl or $C_1-C_4$ alkyl; a cyclohexenyl or cyclopentenyl residue; a phenyl ring which is unsubstituted or substituted by at least one of $C_1-C_4$ alkyl, $C_{1-C4}$ alkoxy, $C_1-C_4$ alkylthio, $C_1-C_4$ alkylsulfinyl, $C_1-C_4$ alkylsulfonyl, trifluoromethyl, nitro, amino, hydroxy, cyano, mercapto, carboxy, phenoxy, benzyloxy, phenyl, benzol, carboxy-$C_1-C_4$-alkyl, methylenedioxy, ethylenedioxy, fluorine, chlorine, bromine, iodine, carboxymethoxy, caboxyethoxy, acetoxy, acetyl, propionyl, a $NR^6R^7$ group, wherein $R^6$ is hydrogen, $C_1-C_4$ alkyl or benzyl and $R^7$ is hydrogen, $C_1-C_4$ alkyl, benzyl, phenyl or benzoyl; wherein an aromatic ring of $R^6$ or $R^7$ is unsubstituted or substituted by at least one of halogen, hydroxy or $C_1-C_4$ alkoxy, or $R^7$ is an α- or β-naphthyl ring which is unsubstituted or substituted by at least one of methyl, hydroxy, methoxy, carboxy, methoxycarbonyl, ethoxycarbonyl, cyano, acetyl, chlorine or bromine or a tetrahydronaphthyl residue;
- or a physiologically tolerated salt or ester thereof, or an optically active form thereof.

6. The compound of claim 5, wherein
- A is an alkylene claim of 8–14 carbon atoms;
- A' is a valency bond or a vinylene or acetylene group;
- B is a valency bond, oxygen, a methylene group, sulfur, or a sulfoxide or sulfonyl group; and
- W is a $C_3-C_8$ cycloalkyl residue or a substituted or unsubstituted phenyl residue.

7. The compound of claim 6, wherein A is an alkylene claim of 10–12 carbon atoms.

8. The compound of claim 6, wherein W is 4-chlorphenyl, 4-methylthiophenyl, 4-$C_1-C_4$-alkylphenyl or 4-methylsulfonylphenyl.

9. The compound of claim 5, wherein the compound is
2,2-dichloro-12-(4-methyl-phenoxy)-dodecanoic acid,
2,2-dichloro-12-(4-methylsulfenylphenyl)-dodecanoic acid,
2,2-dichloro-12-phenyoxy-dodecanoic acid,
2,2-dichloro-12-(4-chlorophenoxy)-dodecanoic acid,
2,2-dichloro-14-phenyl-tetradecanoic acid,
2,2-dichloro-13-cyclohexyl-tridecanoic acid, or
2,2-dichloro-15-cyclohexyl-pentadecanoic acid.

10. The compound of claim 5, wherein the compound is 2,2-dichloro-12-(4-chlorophenyl)-dodecanoic acid.

11. A pharmaceutical composition suitable for the treatment of diabetes mellitus, comprising a compound of claim 5 together with a pharmaceutically acceptable carrier therefor.

12. A pharmaceutical composition suitable for the treatment of diabetes mellitus, comprising a compound of claim 6 together with a pharmaceutically acceptable carrier therefor.

13. A pharmaceutical composition suitable for the treatment of diabetes mellitus, comprising a compound of claim 7 together with a pharmaceutically acceptable carrier therefor.

14. A pharmaceutical composition suitable for the treatment of diabetes mellitus, comprising a compound of claim 8 together with a pharmaceutically acceptable carrier therefor.

15. A pharmaceutical composition suitable for the treatment of diabetes mellitus, comprising a compound of claim 9 together with a pharmaceutically acceptable carrier therefor.

16. A pharmaceutical composition suitable for the treatment of diabetes mellitus, comprising a compound of claim 10 together with a pharmaceutically acceptable carrier therefor.

* * * * *